United States Patent [19]

Frickel et al.

[11] Patent Number: 4,459,404

[45] Date of Patent: Jul. 10, 1984

[54] AMIDES OF RETINOIC ACIDS WITH 5-AMINO TETRAZOLE

[75] Inventors: Fritz-Frieder Frickel, Deidesheim; Axel Nuerrenbach, Gruenstadt, both of Fed. Rep. of Germany

[73] Assignee: BASF Aktiengesellschaft, Fed. Rep. of Germany

[21] Appl. No.: 321,728

[22] Filed: Nov. 16, 1981

Related U.S. Application Data

[63] Continuation of Ser. No. 224,643, Jan. 13, 1981, abandoned.

[30] Foreign Application Priority Data

Jan. 25, 1980 [DE] Fed. Rep. of Germany ....... 3002545

[51] Int. Cl.³ .................... C07D 257/06; A61K 31/41
[52] U.S. Cl. ...................................... 548/253; 424/269
[58] Field of Search ........................ 548/253; 542/421

[56] References Cited

U.S. PATENT DOCUMENTS 3,256,248  6/1966  Lee ........................................ 548/253
3,950,418  4/1976  Bollag et al. ......................... 260/404

FOREIGN PATENT DOCUMENTS 2102586  8/1971  Fed. Rep. of Germany .
2300107  7/1974  Fed. Rep. of Germany .

OTHER PUBLICATIONS

Staab et al., Liebigs Ann., 654 (1962), pp. 129 et seq.
Monographic: G. Plewig and A. M. Klingman, Acne-Morphogenesis and Treatment, Springer-Verlag, Heidelberg 1975.
M. B. Sporn "Chemoprevention of Cancer with Retinoids" Federation Proceedings 38 (1979), pp. 2528-2534.
S. D. Harrison, Nature 269 (1977), pp. 511-512.

Primary Examiner—Paul M. Coughlan, Jr.
Assistant Examiner—D. B. Springer
Attorney, Agent, or Firm—Keil & Weinkauf

[57]  ABSTRACT

5-Amino-tetrazole derivatives of retinoic acids and their physiologically tolerated salts, processes for their preparation and pharmaceutical formulations which contain these derivatives and salts and which may, in particular, be used in the treatment of dermatoses.

3 Claims, No Drawings

AMIDES OF RETINOIC ACIDS WITH 5-AMINO TETRAZOLE

This is a continuation, of application Ser. No. 224,643, filed Jan. 13, 1981 now abandoned.

The present invention relates to 5-aminotetrazole derivatives of retinoic acids and their physiologically tolerated salts, processes for their preparation and pharmaceutical formulations which contain these derivatives and salts and which may, in particular, be used in the treatment of dermatoses.

It is known, for example, from German Laid-Open Application DOS No. 2,102,586, that amides, which may or may not be substituted at the amide nitrogen, of all-E-retinoic acid exhibit a pharmacological action in the topical and systemic therapy of neoplasias, acne, psoriasis and other dermatological disorders. Furthermore, all-E-retinoic acid amides containing higher alkyl radicals, cyclic amide radicals and, in particular, substituted anilide radicals have been disclosed for similar applications, for example in German Laid-Open Application DOS No. 2,300,107.

It is known to those skilled in the art that the above retinamides do not always have a satisfactory action. A particular disadvantage is that the intensity of the action is too low, making it appear that these compounds are not very suitable for use in the topical and systemic therapy of neoplasias, acne, psoriasis and other dermatological disorders. Accordingly, it is not surprising that none of the compounds described in German Laid-Open Applications DOS No. 2,102,586 and DOS No. 2,300,107 is actually used as a drug. In contrast, all E-retinoic acid (vitamin-A-acid) is known to be used in a commercial formulation, for example for the control of acne, but in that case the disadvantages mentioned below must be accepted.

It is an object of the present invention to provide more active retinoids.

We have found that compounds of the formula (I)

(I)

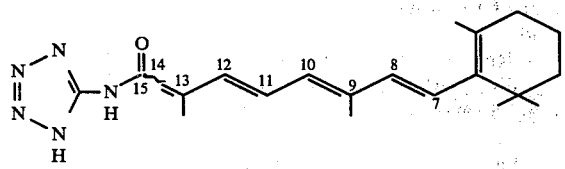

where the squiggly bond between carbon atoms 14 and 15 is an all-E-link or 13-Z-link, and their physiologically tolerated salts, exhibit valuable pharmacological properties.

Accordingly, the compounds according to the invention are all-E-N-(tetrazol-5-yl)-retinamide and 13-Z-N-(tetrazol-5-yl)-retinamide.

For example S. D. Harrison in Nature, 269 (1977), 511–512 reports, concerning the toxic effects of retinoic acid, that even slightly increased doses cause severe damage to the organism, for example with symptoms of hypervitaminosis-A.

The above disadvantages can be avoided by the novel compounds of the formula (I), since these have a relatively low cellular toxicity and a high pharmacological activity, and consequently a particularly favorable therapeutic index.

The practical usefulness of retinoids in pharmacology however depends on more than just the pharmacological activity and the concomitant toxicity. A very critical factor is the pharmacokinetic behavior of the individual active compounds. For example, when employing a retinoid it is a disadvantage if, in the course of the treatment, the metabolism causes the compound to be stored in individual organs at such high concentrations that toxic side-effects arise. For this reason, for example, retinol and retinyl acetate are ruled out for use in therapy, since in both cases an intolerably high retinoid concentration in the liver leads to severe and irreversible damage to the organ.

Such disadvantages can be avoided by the use of the novel compounds, since these, when administered repeatedly, lead to an increase in retinoid concentration which is desired and specific to the particular organ, without being accompanied by a substantial increase in the retinoid concentration in the liver.

It is to be noted that the compounds represented by formula (I) contain a tautomeric hydrogen and that accordingly they can exist in the 1H-tetrazol-5-yl form (formula I) and/or the 2H-tetrazol-5-yl form (formula Ia).

(I)

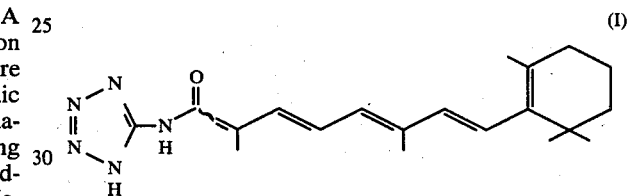

(Ia)

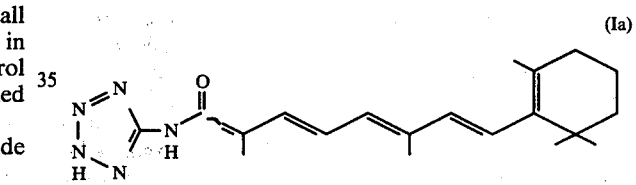

The invention encompasses both forms; for reasons of simplicity, formula (I) will be employed in the text which follows.

The novel compounds of the formula (I) are prepared by a method wherein a reactive retinoic acid derivative of the formula (II)

(II)

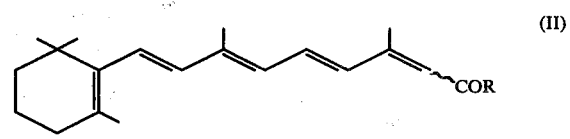

where the squiggly bond between carbon atoms 14 and 15 is an all-E-link or 13-Z-link and R is a suitable leaving group, is reacted, in a conventional manner, with 5-aminotetrazole, advantageously in a solvent and in the presence or absence of an acid acceptor, and, if desired, the resulting compound is converted to a physiologically tolerated salt by means of a basic compound.

The leaving group R is preferably a halogen atom, especially chlorine or bromine, preferably chlorine, or in an N-oxysuccinimide radical.

The reaction is carried out at from −40° C. to 50° C., under atmospheric pressure or in a closed vessel under superatmospheric pressure.

Advantageously, the reaction is carried out in the presence of an inert diluent or solvent, for example a lower saturated dialkyl ether, dialkyl glycol ether or cyclic ether, eg. diethyl ether, ethyl tert.butyl ether, 1,2-dimethoxyethane, tetrahydrofuran or dioxane, an aromatic hydrocarbon, eg. benzene or an alkylbenzene, such as toluene or xylene, a saturated aliphatic hydrocarbon, eg. hexane, heptane or isooctane, a lower aliphatic ketone, eg. acetone, methyl ethyl ketone or methyl isobutyl ketone or a dialkylformamide, eg. dimethylformamide or diethylformamide, or a mixture of the said solvents.

Preferred solvents to use in reacting a retinoic acid chloride of the formula II with 5-amino-tetrazole are ethers, especially diethyl ether and tetrahydrofuran, and dialkylformamides, especially dimethylformamide, the preferred reaction temperatures being from −20° C. to 30° C.

When using a retinoic acid halide, the reaction is preferably carried out in the presence of a base as the acid acceptor. Suitable bases include alkali metal carbonates and bicarbonates, especially sodium and potassium carbonate and bicarbonate, organic tertiary bases, eg. pyridine and lower trialkylamines, such as trimethylamine or triethylamine. The base is employed in the stoichiometric amount or in slight excess over the retinoic acid halide.

The novel compounds of the formula (I) may also be prepared by a method wherein all-E-retinoic acid or 13-Z-retinoic acid is condensed with 5-aminotetrazole in a solvent, in the presence of a dehydrating agent which activates the carboxyl group, and, if desired, the resulting compound is converted to a physiologically tolerated salt by means of a base.

Suitable dehydrating activating reagents are those conventionally employed in peptide synthesis, as described, for example, by Schröder and Lübke in "The Peptides", Volume I, Academic Press, N.Y., 1965, pages 77–128. The general principle of the synthesis is that the carboxyl group is activated, for example by treatment with a carbodiimide, eg. N,N'-dicyclohexylcarbodiimide, or by intermediate formation of the acid azide, of a mixed anhydride (for example with a carbonic acid monoester), an activated ester (for example the p-nitrophenyl ester) or a heterocyclic amide (for example an imidazolide) of the corresponding retinoic acid.

Treating a compound, activated at the carboxyl group, with 5-aminotetrazole leads to the novel compounds. The activation and linking reactions are carried out in an inert solvent, preferably in N,N-dimethylformamide, tetrahydrofuran, dioxane, methylene chloride, nitromethane, acetonitrile, dimethylsulfoxide, N,N-dimethylacetamide or hexamethylphosphortriamide.

Both steps of the reaction, ie. the reaction of the acid with the coupling agent and the reaction of the activated intermediate with 5-aminotetrazole, are carried out at from 20° to 100° C. The condensation reaction can either be carried out stepwise by isolating the activated intermediate before adding the 5-aminotetrazole, or, advantageously, by causing the reactants to react successively without isolating an intermediate stage.

In a preferred linking method, N,N-carbonyldiimidazole is used.

This preferred reaction is carried out with 5-aminotetrazole in one of the above inert solvents, regardless of whether a two-step or one-step procedure is employed. The preferred solvent is N,N-dimethylformamide and preferably both steps are carried out at from 20° to 60° C.

The intermediate all-E-retinoic acid imidazolide is described, for example, by Staab and Bräunling in Liebigs Ann. 654 (1962), 129.

Mixtures of the all-E-isomer and 13-Z-isomer may also be used as starting compounds of the formula (II), since the industrial preparation of these compounds may result in such mixtures. In such cases, the resulting mixture of novel compounds of the formula (I) can be quantitatively analyzed by high pressure liquid chromatography or by means of the $^{13}$C-NMR spectrum and pure isomers can, if desired, be isolated by fractional crystallization or chromatography, for example chromatography on a silica gel column or preparative high pressure liquid chromatography.

The novel compounds have an acidic hydrogen and can therefore be converted, in a conventional manner, to physiologically tolerated, readily water-soluble salts with bases. Examples of suitable salts are ammonium salts, alkali metal salts, especially sodium, potassium and lithium salts, alkaline earth metal salts, especially calcium and magnesium salts, and salts with suitable organic bases, such as lower alkylamines, eg. methylamine or ethylamine, substituted lower alkylamines, especially hydroxy-substituted alkylamines, eg. diethanolamine, triethanolamine or tris-(hydroxymethyl)aminomethane, piperidine and morpholine.

Because of their pharmacological properties, the novel compounds and their physiologically tolerated salts may be used in the topical and systemic therapy of dermatological disorders accompanied by pathologically modified keratinization, The pharmacological effects can be demonstrated in, for example, the following assays: the novel compounds reverse the keratinization which occurs on hamster tracheal tissue in vitro after vitamin A deficiency. This keratinization is inhibited, after initiation by chemical compounds, through the use of high energy radiation, or after viral cell transformation, through the use of the novel compounds of the formula (I). The method is described in Cancer Res. 36 (1976), 964–972, Nature 250 (1974), 64–66 and Nature 253 (1975), 47–50.

The data which follow substantiate the superior effect of the novel compounds compared to vitamin-A-acid.

1. Reversal of keratinization in tracheal organ culture by all-E-N-(tetrazol-5-yl)-retinamide and 13-Z-N-(tetrazol-5yl)-retinamide to demonstrate the anti-tumor action.

This assay measures the intrinsic ability of the novel compounds to control epithelial cell differentiation. The significant predictive value of this screening procedure for the potential use of a novel retinoid in the prevention of epithelial tissue tumors is generally accepted. At the same time it is known that any in vitro test system has disadvantages for the prediction of in vivo activity. Apart from these fundamental limitations, the tracheal organ culture assay is one of the most valuable procedures for evaluating the biological activity of a novel retinoid.

The assay procedure determines the ability of the two compounds to reverse keratinization in a defined in vitro system. Tracheas from hamsters in a very early stage of vitamin A deficiency were placed in organ culture. At that time, the animals were 29–30 days old (having been weaned at 21 days) and were still gaining some weight. Their average weight was 47–52 g. Their tracheal epithelium was generally low columnar or cuboidal, with only occasional patches of squamous metaplasia. Each trachea was opened from the larynx to the carina along the membranous dorsal wall and placed in culture in a serum-free medium (CMRL-1066 supplemented with crystalline bovine insulin, 1.0 μg/ml; hydrocortisone hemisuccinate, 0.1 μg/ml; glutamine, 2 mM; penicillin, 100 units/ml; and streptomycin, 100 μg/ml). The cultures were gassed with a mixture of 50% of oxygen, 45% of nitrogen and 5% of carbon dioxide. The culture dishes were rocked through 35.5–36.0 degrees to contact the tracheas with both gas and medium. All tracheas were maintained in medium containing no retinoid for the first 3 days. At the end of the 3 days, some tracheas were harvested. Almost all of these tracheas had significant squamous metaplasia. The remaining tracheas were then divided into groups which were treated with either (a) the test substance dissolved in spectroscopically pure dimethylsulfoxide; the final concentration of dimethylsulfoxide in the culture medium was never greater than 0.1%, or (b) an equivalent amount of dimethylsulfoxide without other additives.

The culture medium was changed three times a week and all of the remaining tracheas were harvested at the end of 10 days in culture. The tracheas were fixed in 10% strength buffered formaldehyde solution and embedded in paraffin. Cross-sections of 5 μm thickness were taken through the mid-portion, stained with hexatoxylin and eosin and then examined under a microscope for the presence of keratin and keratohyaline, both of which were found in approximately 90% of all the control cultures that had been kept without test substance. Dose-response curves of the novel compounds were made. Table 1 below shows the extrapolated molar doses which were effective in suppressing keratinization in one-half of the cultures (ED 50%).

TABLE 1

|  | $ED_{50}$ [mole/l] | Number of cultures |
| --- | --- | --- |
| all-E-N—(tetrazol-5-yl)-retinamide | $1 \times 10^{-10}$ | 65 |
| 13-Z-N—(tetrazol-5-yl)-retinamide | $2 \times 10^{-10}$ | 63 |
| all-E-retinoic acid | $3 \times 10^{-11}$ | 65 |

2. Comparative toxicity of all-E-N-(tetrazol-5-yl)-retinamide and 13-Z-N-(tetrazol-5-yl)-retinamide.

The novel compounds are significantly less toxic than all-E-retinoic acid when administered orally to rats. Both retinoids were administered to rats in massive doses, and inhibition of growth and lethality were observed over a two-week period (Table 2).

(a) Male Sprague-Dawley CD rats from Charles River (50–75 g) were randomized and weighed daily for one week before the start of the experiment. At the beginning of the toxicological screen the animals weighed 95–110 g.

(b) The vehicle for the test substances was corn oil containing 4% of chloroform. The dose was 25 μmole of test substance/day, in 0.5 ml of vehicle.

TABLE 2

|  | Proportion of survivors | | Average weight+ | |
| --- | --- | --- | --- | --- |
|  | Day 6 | Day 11 | Day 6 | Day 11 |
| all-E-N—(tetrazol-5-yl)-retinamide | 3/4 | 3/4 | 124 ± 6 | 155 ± 4 |

TABLE 2-continued

|  | Proportion of survivors | | Average weight+ | |
| --- | --- | --- | --- | --- |
|  | Day 6 | Day 11 | Day 6 | Day 11 |
| 13-Z-N—(tetrazol-5-yl)-retinamide | 2/5 | 2/5 | 122 ± 18 | 140 ± 27 |
| all-E-retinoic acid | 3/5 | 0/5 | 95 ± 2 | — |
| untreated control group | 5/5 | 5/5 | 140 ± 2 | 182 ± 2 |

+mean with standard deviation

3. Comedolytic activity, as a demonstration of dermatological activity.

0.1-E-N-(Tetrazol-5-yl)-retinamide and 13-Z-N-(tetrazol-5-yl)-retinamide were evaluated for comedolytic activity in a rabbit ear model system.

Comedo formation was induced by topical application (0.5 ml), once daily, of 5% coal tar in Polyan ® (an ester of lanolin alcohol and linoleic acid, from Amerchol Corp., USA) to both ears of albino rabbits on 5 successive days per week, for two weeks. Following this, the test substance, in a 70:30 volume/volume alcohol:propylene glycol mixture, was applied topically, in an amount of 0.5 ml, to the inner surface of one ear of each rabbit once daily on 5 consecutive days per week, for two weeks. The contra-lateral ear of each rabbit served as an untreated control.

Following a subsequent treatment (~72 hours) with the test substance, the rabbits were sacrificed. A sample of skin, of about 6 cm², was removed from the pinna of each ear just external to the auditory canal and was divided into pieces of about 1 cm².

These pieces of skin were immersed in water at 60° C. for 2 minutes. The epidermis was carefully peeled off using the flat end of a spatula and fine forceps, and was placed on a microscope slide, with the dermal side facing upward. After overnight airdrying, the slide was examined under the stereomicroscope. Follicular extensions of horny material remain intact. Comedones show up as discrete, uniformly shaped, cylindrical to global horny masses, whose size and number are proportional to the potency of the test compound.

The comedolytic effect was determined by the decrease in the number of comedones in comparison with the control ear.

TABLE 3

|  | % concentration | N (number of animals) | % comedolytic activity |
| --- | --- | --- | --- |
| all-E-N—(tetrazol-5-yl)-retinamide | 0.025 | 6 | 35.1 |
| 13-Z-N—(tetrazol-5-yl)-retinamide | 0.1 | 6 | 39.4 |
| all-E-retinoic acid | 0.05 | 6 | 58.3 |

The numerical data show that the novel compounds exhibit a pronounced comedolytic activity, even though somewhat less than that of all-E-retinoic acid, in the rabbit ear model system.

4. Topical tolerance study of the test substances

Six New Zealand white male rabbits were used in each study. Sites, each about 6 cm² in size, were shaved on the dorsal trunk of each test animal. The test substances were dissolved in a 70:30 volume/volume alcohol:propylene glycol mixture and 0.2 ml of the solution was applied topically from an automatic micropipette by gentle inunction to a pre-designated site twice daily, with an interval of six hours, for nine successive days.

All sites were subjectively evaluated for erythema and scaling at the beginning of the test and before each morning application. A numerical grading scale of 0 to 3 was used (0=no reaction, 1=mild, 2=moderate, 3=severe). The mean degree of erythema and scaling indicates the relative irritating capacity of the test substances, compared to all-E- and 13-Z-retinoic acid and to a vehicle control test.

TABLE 4

9-day study of dermal irritation after repeated application

|  | % concentration | N number of animals | mean erythema | scaling | Rating erythema | scaling |
|---|---|---|---|---|---|---|
| all-E-N—(tetrazol-5-yl)-retinamide | 0.025 | 6 | 0.8 | 0 | mild | none |
| 13-Z-N—(tetrazol-5-yl)-retinamide | 0.1 | 6 | 0.5 | 0.1 | mild | none |
| all-E-retinoic acid | 0.025 | 6 | 2.3 | 1.9 | moderate | moderate |
| 13-Z-retinoic acid | 0.1 | 6 | 3.0 | 3.0 | severe | severe |

Accordingly, the invention also relates to therapeutic agents for topical and systemic use, which contain a compound of the formula (I) as the active compound, in addition to conventional vehicles or diluents, and the use of a compound of the formula (I) for the preparation of a medicament.

The therapeutic agents and formulations are prepared in a conventional manner, for example by mixing the active compound with the conventional liquid or solid vehicles or diluents and the conventionally used pharmaceutical auxiliaries, in accordance with the desired route of administration, and employing dosages appropriate to the particular application.

The formulations may be administered perorally, parenterally or topically. Examples of appropriate formulations are tablets, film tablets, dragees, capsules, pills, powders, solutions, suspensions, infusion solutions, injection solutions, pastes, ointments, gels, creams, lotions, powders, solutions, emulsions and sprays.

The concentration of the novel compounds in the therapeutic agents is from 0.001 to 1%, preferably from 0.001 to 0.1%, for local application; for systemic use, an individual dose preferably contains from 0.1 to 50 mg of the novel compound, and one or more doses may be administered daily, depending on the nature and severity of the disorder.

Examples of conventionally used pharmaceutical auxiliaries are alcohols, eg. isopropanol, oxyethylated castor oil, oxyethylated hydrogenated castor oil, polyacrylic acid, glycerol monostearate, paraffin oil, white petroleum jelly, lanolin, polyethylene glycol 400, polyethylene glycol 400-stearate and oxyethylated fatty alcohols in the case of local application, and lactose, propylene glycol, ethanol, starch, talc and polyvinylpyrrolidone in the case of systemic administration. The formulations may contain an antioxidant, for example tocopherol, butylated hydroxyanisole or butylated hydroxytoluene, and/or flavor improvers, stabilizers, emulsifiers, lubricants and the like. All the materials used in the preparation of the pharmaceutical formulation must be toxicologically safe and compatible with the active compounds used.

Preparation of the novel compounds

EXAMPLE 1 all-E-N-(tetrazol-5-yl)-retinamide

A solution of 140 millimole of all-E-retinoyl chloride in 500 ml of tetrahydrofuran is added dropwise, in the course of 10 minutes, to a suspension of 15.3 g of anhydrous 5-aminotetrazole and 15 ml of pyridine in 200 ml of tetrahydrofuran at about 210° C., and the mixture is then stirred for about 20 hours at room temperature. On the following day, the suspension formed is stirred into a mixture of 2 liters of water, 75 ml of concentrated hydrochloric acid and 250 ml of ethanol and the precipitate formed is filtered off and is finally purified by recrystallization from a methylene chloride/tetrahydrofuran/heptane mixture. 27 g of all-E-N-(tetrazol-5-yl)-retinamide, of melting point 228°–230° C., are obtained.

$E_1^1$: 1,129 at 390 nm.

$C_{27}H_{29}ON_5$ (367): calc.: 68.6 C, 8.0 H, 19.1 N; found: 68.6 C, 7.7 H, 19.4 N.

EXAMPLE 2

13-Z-N-(tetrazol-5-yl)-retinamide

Using the method described in Example 1, 7.7 g of 5-aminotetrazole, 7.5 ml of pyridine in 200 ml of tetrahydrofuran and 70 millimoles of 13-Z-retinoyl chloride in 250 ml of tetrahydrofuran give 11 g of 13-Z-N-(tetrazol-5-yl)-retinamide, of melting point 215°–217° C.

$E_1^1$: 1,116 at 390 nm.

$C_{27}H_{29}ON_5$ (367): calc.: 68.6 C, 8.0 H, 19.1 N; found: 68.8 C, 7.9 H, 19.3 N.

EXAMPLE 3 all-E-N-(tetrazol-5-yl)-retinamide

A mixture of 3 g of all-E-retinoic acid and 1.9 g of N,N'-carbonyldiimidazole in 50 of N,N'-dimethylformamide is gently warmed on a steam bath for 15 minutes and is then left to stand for 45 minutes at room temperature. 1 g of 5-aminotetrazole is then added and the mixture is heated for 1 hour at about 50° C., allowed to cool and filtered into 0.3 liter of water. The whole is brought to pH 1 with hydrochloric acid. The solid is filtered off and worked up, as described in Example 1, to give analytically pure all-E-N-(tetrazol-5-yl)-retinamide.

EXAMPLE 4

Sodium salt of all-E-N-(tetrazol-5-yl)-retinamide

About 1 mole equivalent of aqueous sodium hydroxide solution is added to a suspension of 1 g of all-E-N-(tetrazol-5-yl)-retinamide in 200 ml of water and 30 ml of tetrahydrofuran. The reaction mixture is stirred for several hours and then filtered. The salt given in the title is obtained, in a hydrated form, by freeze-drying the filtrate.

If, in this method, sodium hydroxide is replaced by other bases, for example by ethanolamine, ethylenediamine, diethanolamine, triethanolamine or tris(hydroxymethyl)-aminomethane, the corresponding amine salts are obtained, which in some cases can be used as aqueous solutions, without isolating the active compound.

Examples of suitable pharmaceutical formulations or drug/vehicle combinations for external application are given below:

EXAMPLE I

| Solution | |
|---|---|
| Na salt of all-E-N—(tetrazol-5-yl)-retinamide | 0.25 g |
| oxyethylated hydrogenated castor oil (Cremophor RH 40, from BASF AG, Ludwigshafen) | 35.0 g |
| polyethylene glycol 400 | 35.0 g |
| oxyethylated castor oil (Softigen 767, from Chemische Werke Witten) | 10.0 g |
| demineralized water | add 100.0 g |

The Cremophor RH 40 and Softigen 767 are mixed and heated to 70° C. The active compound is dissolved in this mixture, whilst stirring, and the polyethylene glycol 400 is added. The solution is then added slowly to water at 40° C. The finished solution is filtered and, for example, packed in 100 ml bottles.

EXAMPLE II

| Cream | |
|---|---|
| all-E-N—(tetrazol-5-yl)-retinamide | 0.1 g |
| butylhydroxytoluene | 0.1 g |
| glycerol monostearate | 11.0 g |
| polyethylene glycol 400-stearate | 6.0 g |
| oxyethylated fatty alcohol | 4.0 g |
| medicinal paraffin | 10.0 g |
| p-hydroxybenzoic acid ester (Nipasteril, from Nipalaboratorium, Hamburg) | 0.2 g |
| perfume oil | 0.1 g |
| demineralized water | ad 100.0 g |

The fats are melted and the active compound, in the form of an extremely fine powder, and the butylhydroxytoluene are dispersed in the melt at 65° C., by stirring (dispersion I). The water is boiled up with the Nipasteril and the mixture is cooled to 65° C. (solution II). Solution II is emulsified, a little at a time, in dispersion I, by thorough stirring. When the mixture has cooled to 45° C., the perfume oil is added and the emulsion is cooled to room temperature, whilst stirring. The finished cream is packed in tubes possessing an internal protective lacquer.

EXAMPLE III

| Gel | |
|---|---|
| all-E-N—(tetrazol-5-yl)-retinamide | 0.01 g |
| butylhydroxytoluene | 0.1 g |
| oxyethylated castor oil (Cremophor E1, from BASF AG, Ludwigshafen) | 35.0 g |
| isopropanol | 20.0 g |
| polyacrylic acid (Carbopol from Goodrich, Hamburg) | 1.5 g |
| triethanolamine | 0.002 g |
| p-hydroxybenzoic acid ester (Nipasteril, from Nipalaboratorium, Hamburg) | 0.2 g |
| demineralized water | ad 100.0 g |

The Cremophor E1 is heated to 60° C., the active compound and the butylhydroxytoluene are dissolved therein by stirring, and the isopropanol, in which the Nipasteril has been dissolved, is admixed (solution I). The Carbopol is dispersed in water, by vigorous stirring (dispersion II). Dispersion II is admixed, a little at a time, to solution I, with thorough stirring. The pH of the mixture is brought to 4.5 with triethanolamine. The finished gel is packed in tubes possessing an internal protective lacquer.

The following are examples of formulations or active compound/vehicle combinations particularly suitable for systemic use:

EXAMPLE IV

| Drops | |
|---|---|
| 13-Z-N—(tetrazol-5-yl)-retinamide | 0.1 g |
| propylene glycol | 25.0 g |
| ethyl alcohol | ad 50.0 g |

The ethyl alcohol and propylene glycol are mixed and the active compound is dissolved therein by stirring and heating to 35° C. The solution is filtered and then packed in dark dropper bottles.

EXAMPLE V

| Hard gelatin capsules | |
|---|---|
| 13-Z-N—(tetrazol-5-yl)-retinamide | 1 mg |
| lactose | ad 0.25 g |

The constituents are passed through a sieve, mixed and filled into size 2 hard gelatin capsules on a suitable capsule filling and sealing machine.

We claim:

1. A compound of the formula (I)

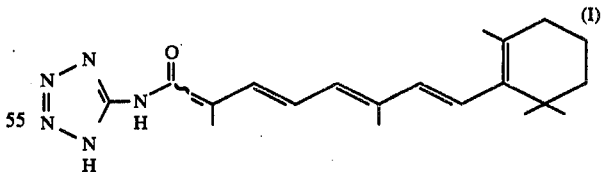

where the squiggly bond between carbon atoms 14 and 15 is an all-E-link or 13-Z-link, and its physiologically tolerated salts.

2. all-E-N-(Tetrazol-5-yl)-retinamide and its physiologically tolerated salts.

3. 13-Z-N-(Tetrazol-5-yl)-retinamide and its physiologically tolerated salts.

* * * * *